United States Patent [19]

Basarab

[11] Patent Number: 5,128,348

[45] Date of Patent: Jul. 7, 1992

[54] BICYCLO(3.1.0)HEXANE AMINES AND BICYCLO(4.1.0)-HEPTANE AMINES AS AGRICULTURAL FUNGICIDES

[75] Inventor: Gregory S. Basarab, Hockessin, Del.

[73] Assignee: E. I. Du Pont de Nemours and Company, Wilmington, Del.

[21] Appl. No.: 580,473

[22] Filed: Sep. 12, 1990

[51] Int. Cl.$^5$ .................. A61K 31/445; C07D 413/00; C07D 295/14; C07D 409/00

[52] U.S. Cl. ................................ 514/320; 514/233.5; 514/233.8; 514/254; 514/307; 514/321; 514/324; 514/337; 514/338; 514/422; 514/432; 514/438; 514/443; 514/456; 514/469; 514/470; 544/145; 544/147; 544/149; 544/151; 544/152; 544/153; 544/163; 544/374; 544/376; 544/379; 544/392; 544/394; 544/395; 546/139; 546/141; 546/142; 546/144; 546/207; 546/212; 546/213; 546/214; 546/215; 546/216; 546/219; 546/196; 546/268; 546/283; 546/284; 546/329; 546/347; 549/60; 549/424; 549/475; 549/476; 549/480; 564/297

[58] Field of Search ............... 544/145, 147, 149, 151, 544/152, 153, 163, 374, 376, 379, 392, 394, 395; 546/139, 141, 142, 144, 268, 283, 284, 329, 347, 207, 212, 213, 214, 215, 216, 219, 196; 548/517, 527, 542, 543, 544, 545; 549/60, 424, 475, 476, 480; 564/297; 71/88, 90, 92, 94, 95; 514/233.5, 233.8, 254, 307, 320, 321, 324, 337, 338, 422, 432, 438, 443, 456, 469, 470

[56] References Cited

FOREIGN PATENT DOCUMENTS 0259977 3/1988 European Pat. Off. .
278311A 8/1988 European Pat. Off. .
2216120 10/1989 United Kingdom .

OTHER PUBLICATIONS

Diery et al., Chem. Abst. 95-61464n (1981) eq. EP-025997 cited in spec.
Berg et al., CA 110-38874r (1989) eq. EP-278311 cited in spec.
Urch et al., CA 112-118637x (1990) eq. UK-2,216,120 cited in spec.

Primary Examiner—Cecilia Shen

[57] ABSTRACT

Certain hexane and heptane amines including geometric and stereoisomers, agricultural compositions containing them and their use as fungicides.

9 Claims, No Drawings

BICYCLO(3.1.0)HEXANE AMINES AND BICYCLO(4.1.0)-HEPTANE AMINES AS AGRICULTURAL FUNGICIDES

BACKGROUND OF THE INVENTION

EP0259977 claims fungicidal compounds of the formula wherein:
- $R^1$, $R^2$ and $R^3$ are independently H, halogen or $C_1$–$C_4$ alkyl;
- $R^4$ is H or $C_1$–$C_4$ alkyl;
- $R^5$ and $R^6$ are $C_1$–$C_4$ alkyl or $R^5$ and $R^6$ together with the adjacent nitrogen atom form a heterocyclic ring which may contain an additional heteroatom;
- X and Y are H, halogen, alkyl, cycloalkyl, cycloalkylalkyl, alkenyl, alkynyl, aryl, aralkyl, alkoxy, aryloxy or a substituted Si; and
- Q and Z are optionally-substituted alkyl groups not containing any fused three-membered rings.

EP 278311-A claims fungicidal compounds of the general formula wherein:
- $R^1$ is optionally substituted aryl, heteroaryl, cycloalkyl, tetrahydronaphthyl or decahydronaphthyl;
- $R^2$ is H or $CH_3$; and
- $R^3$ and $R^4$ are H, alkyl, alkenyl, alkynyl, alkoxyalkyl, dialkoxyalkyl, hydroxyalkyl, hydroxyalkoxyalkyl, dioxolanylalkyl, oxolanylalkyl, dioxanylalkyl or optionally substituted cycloalkylalkyl, cycloalkyl, aralkyl, aralkenyl or aryl, or $NR^3R^4$ is an optionally substituted saturated ring optionally containing other heteroatoms.

GB 2,216,120 discloses fungicidal compounds of the formula wherein:
- $R^1$–$R^8$ are H or (halo)alkyl;
- $R^9$ and $R^{10}$ are (halo)alkyl;
- $NR^9R^{10}$ is heterocyclyl; and
- X is H, halogen, (halo)alkyl, cycloalkyl, alkenyl, alkynyl, aryl, aralkyl, alkoxy, aryloxy or silyl.

None of these publications disclose the compounds of the instant application.

SUMMARY OF THE INVENTION

This invention pertains to compounds of the Formula I including all geometrical isomers but restricted to the stereoisomers in which $R^1$ and $NR^5R^6$ are trans- to one another, agricultural compositions containing them and their use as fungicides.

wherein:
- n is 1 or 2;
- m is 0 or 1;
- p is 0 or 1;
- Q is C, O or S;
- Y is O or $CR^6R^7$;
- $R^1$ is $C_4$–$C_{10}$ alkyl, $C_4$–$C_{10}$ alkenyl, $C_4$–$C_{10}$ alkynyl, $C_4$–$C_{10}$ cyanoalkyl, $C_3$–$C_{10}$ cycloalkyl optionally substituted with $C_1$–$C_6$ alkyl, 2-thienyl substituted with $R^8$ and $R^9$, or $R^1$ is phenyl substituted with $R^8$ and $R^9$, or $R^1$ is styryl substituted with $R^8$ and $R^9$, or $R^1$ is

- $R^2$, $R^3$, $R^{10}$, and $R^{11}$ are independently H, CN, halogen, $C_1$–$C_4$ alkyl, $C_1$–$C_4$ alkoxy or $C_1$–$C_4$ haloalkyl;
- $R^4$ and $R^5$ are independently $C_1$–$C_6$ alkyl, phenethyl optionally substituted with 1–3 substituents selected from the group consisting of halogen, CN and $C_1$–$C_4$ alkyl, or $R^4$ and $R^5$ may be taken together with the nitrogen to which they are attached to form heterocycles of the formulas:

A-1   A-2   A-3

A-4   A-5

$R^6$ and $R^7$ are independently H, halogen, methyl, methoxy, CN or trifluoromethyl;

$R^8$ and $R^9$ are independently H, halogen, CN, $C_1$-$C_6$ alkyl, $C_1$-$C_6$ cyanoalkyl, $C_1$-$C_6$ haloalkyl, $C_3$-$C_6$ cycloalkyl, $C_3$-$C_6$ cycloalkylmethyl, $C_2$-$C_6$ alkenyl, $C_2$-$C_6$ alkynyl, $C_1$-$C_6$ alkoxy, phenyl optionally substituted with halogen, CN or $C_1$-$C_4$ alkyl, phenoxy optionally substituted with halogen, CN or $C_1$-$C_4$ alkyl, or silicon substituted with any three of the group consisting of $C_1$-$C_4$ alkyl, $C_2$-$C_4$ alkenyl, $C_2$-$C_4$ alkynyl and $C_1$-$C_3$ haloalkyl;

$R^{12}$ and $R^{13}$ are independently H, halogen, CN, $C_1$-$C_4$ alkyl, $C_2$-$C_4$ alkenyl, $C_1$-$C_4$ alkoxy, $C_1$-$C_4$ hydroxyalkyl or phenyl optionally substituted with 1–2 halogen;

$R^{14}$ and $R^{15}$ are independently H, halogen, CN, $C_1$-$C_4$ alkyl or $C_1$-$C_4$ alkoxy;

$R^{16}$ is H, OH, halogen, CN, $C_1$-$C_4$ alkyl or $C_1$-$C_4$ alkoxy;

X is O or $NR^{17}$;

$R^{17}$ is H, OH, $C_1$-$C_3$ alkyl or $C_1$-$C_3$ alkoxy;

Z is O or $CH_2$;

and the agriculturally suitable salts thereof provided that:

1) When m is 1, n is 1;
2) When m is 0 and Q is O or S, Y is $CR^6R^7$;
3) When $R^4$ and $R^5$ are taken together to form heterocycles of the Formula A-5, $R^{12}$ and $R^{13}$ may be substituted at positions 2, 3, 8, 9 or 10 and $R^{14}$, $R^{15}$ and $R^{16}$ may be substituted at positions 4, 5, 6 or 7;
4) When $R^2$ or $R^3$ are halogen or $C_1$-$C_4$ alkoxy, then they must not be substituted on a carbon atom attached to O, S or N;
5) When $R^2$ or $R^3$ is CN, then they must not be substituted at the carbon atom attached to $NR^4R^5$.

Preferred for ease of synthesis and/or fungicidal activity are:

1) A compound of Preferred 1 of the formula:

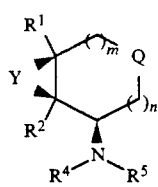

2) A compound of Preferred 1, wherein:
Y is O or $CH_2$;
$R^2$ is H, $CH_3$, $CH_2CH_3$ or CN;
$R^4$ and $R^5$ are taken together to form heterocycles of the formula A-1, A-2, A-3, A-4 or A-5;
$R^8$ and $R^9$ are independently H, halogen, CN, $C_1$-$C_6$ alkyl, $C_1$-$C_6$ cyanoalkyl, $C_1$-$C_6$ haloalkyl or $C_3$-$C_6$ cycloalkyl;
$R^{12}$ and $R^{13}$ are independently H, CN, $C_1$-$C_4$ alkyl, $C_1$-$C_4$ alkoxy or $C_1$-$C_4$ hydroxyalkyl;
$R^{14}$ and $R^{15}$ are independently H, CN or $CH_3$;
$R^{16}$ is H or OH; and
X is O.

3) A compound of Preferred 2 wherein:
m is 0;
n is 1; and
Q is $CH_2$.

4) A compound of Preferred 3 wherein:
$R^4$ and $R^5$ are taken together to form heterocycles of the structures A-1, A-3 or A-4.

5) A compound of Preferred 4 wherein:
$R^1$ is $C_4$-$C_{10}$ alkyl, $C_4$-$C_{10}$ cycloalkyl optionally substituted with $C_1$-$C_6$ alkyl, or $R^1$ is phenyl substituted with $R^8$, or $R^1$ is benzyl substituted with $R^8$ on the aryl moiety;
$R^2$ is H, $CH_3$ or CN;
$R^8$ is H, $C_1$-$C_6$ alkyl, $C_3$-$C_4$ cycloalkyl, CN or $CF_3$; and
$R^{13}$ and $R^{14}$ are independently H or $CH_3$.

6) Specifically preferred is
1-[5-[4-(1,1-dimethylethyl)phenyl]-1-methyl-6-oxabicyclo[3.1.0]hexan-2-yl]-cis-3,5-dimethylpiperidine, [1α,2β,5α].

DETAILED DESCRIPTION OF THE INVENTION

Synthesis

Compounds of Formula I in which p is 1 can be prepared from compounds of Formula I in which p is 0 by oxidation with an appropriate reagent for the conversion of amines to amine-N-oxides. Appropriate reagents include peroxides such as hydrogen peroxide or t-butylhydroperoxide, peracids such as 3-chloroperbenzoic acid or peracetic acid, or Oxone® ($2KHSO_5 \cdot KHSO_4 \cdot K_2SO_4$). The reaction may be catalyzed with group V or group VI metals [see Shong and Fujuret, *J. Org. Chem.* 33, 588 (1968)].

Compounds of Formula I in which p=0 can be prepared by the displacement of a leaving group LG in II with an amine III. Typical values for LG include halides and sulfonates. The reaction is run neat with one to three equivalents of the amine with or without an additional base such as potassium carbonate at temperatures between 25° C. and 150° C. In addition, a solvent such as DMF, tetrahydrofuran or ethanol may be used.

SCHEME 1

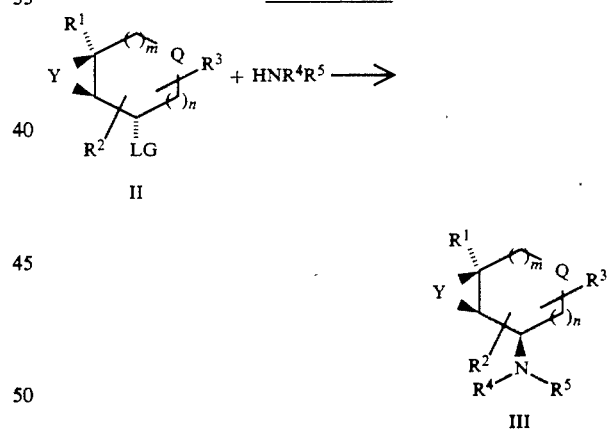

Compounds of Formula Ia wherein $NR^4R^5$ form the heterocycle of Formula A-1 can also be prepared from the corresponding quaternary pyridinium salt of Formulas IVa (where W- is an organic or inorganic counterion such as a sulfonate or halide) by hydrogenation over an appropriate transition metal catalyst (TMC) such as palladium, platinum or rhodium. Typically, the catalyst is deposited over an inert support such as carbon, alumina or calcium carbonate. The hydrogenations are carried out in protic solvents such as ethanol or non-protic solvents such as tetrahydrofuran or ethyl acetate. Pressures of 1–10 atm of hydrogen are required. The hydrogenations are typically run at 25° C. but may be run at temperatures up to 100° C. Optionally, 1-2 equivalents of a base such as potassium carbonate or triethylamine may be added to neutralize the acid produced by the hydrogenation. The salts of Formula IVa can be prepared by displacement of LG in II with a pyridine V. The reaction is run neat with 1 to 100 equivalents of V at temperatures between 25° C. and 100° C. In addition, a solvent such as DMF, dichloroethane or ethanol may be used.

SCHEME 2

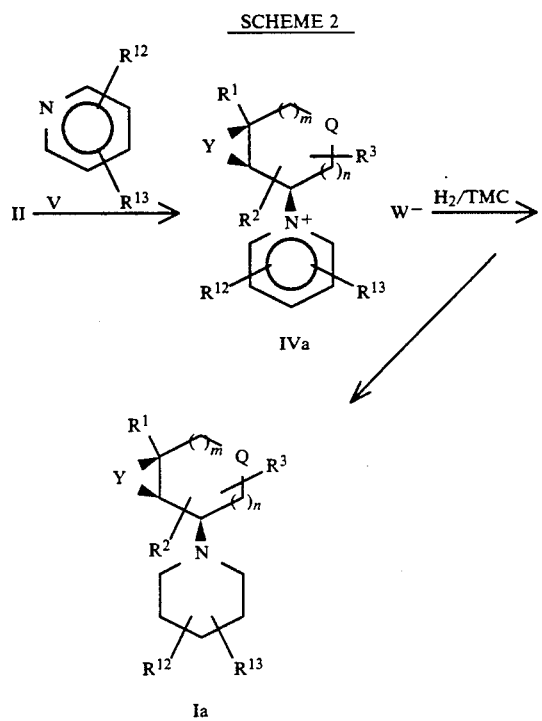

Compounds of Formula Ib where $NR^4R^5$ form the heterocycle of A-2 can be prepared from IVa by reduction with a hydride reagent such as sodium borohydride, sodium cyanoborohydride, tetrabutylammonium cyanoborohydride, or sodium formate. The reductions are run at $-20°$ C. to 100° C. in protic solvents such as ethanol or aprotic solvents such as DMF, tetrahydrofuran or methylene chloride.

SCHEME 3

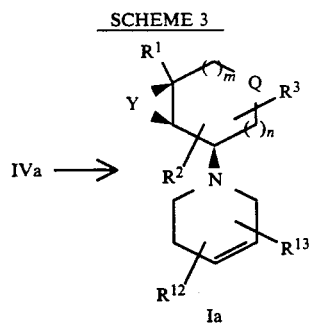

Alternatively, compounds of Formula I can be prepared by reductive amination of compounds of Formula V with amine III. The reactions are run with 1-10 equivalents of the amine and with a reducing reagent such as formic acid, sodium cyanoborohydride or tetrabutylammonium cyanoborohydride. Addition of a protic acid such as HCl or p-toluenesulfonic acid is often useful to catalyze the reductive amination. Reaction temperatures can vary from 0° C. to 100° C. Appropriate solvents include alcohols such as methanol or ethanol, or aprotic solvents such as dimethylformamide or methylene chloride.

SCHEME 4

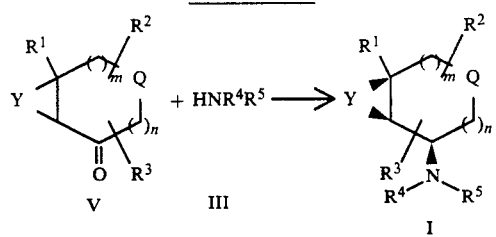

The compounds IIa in which

is a sulfonate can be prepared from an alcohol VI and a sulfonyl chloride (e.g., toluenesulfonyl chloride) or a sulfonic anhydride (e.g., trifluoromethane sulfonic anhydride) and a base such as pyridine or triethylamine in a solvent such as pyridine, methylene chloride or tetrahydrofuran at temperatures between 0° C. and 25° C. Compounds IIb in which Hal is a halogen can be prepared from VI using standard conditions known to one familiar in the art such as treatment with thionyl chloride or phosphorus tribromide. The iodide can be prepared from the chloride or bromide using sodium iodide in acetone or methyl ethyl ketone.

SCHEME 5

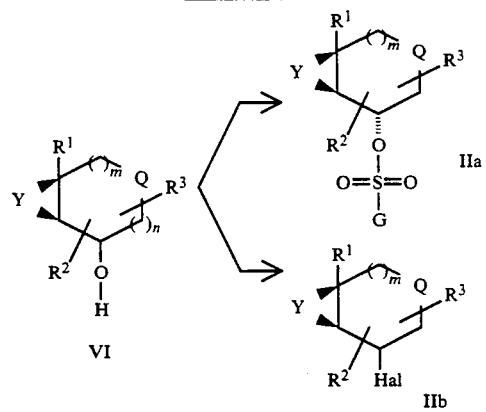

Those skilled in the art will recognize that alcohol VI is interconvertable with compound V if $R^2$ and $R^3$ are not positioned on the alcohol bearing carbon. Alcohols VI can be oxidized to V by methods set out in the literature (see leading references in J. March, *Advanced Organic Chemistry*, 3rd Ed., J. Wiley and Sons, New York, N.Y., 1985, pp. 1057-1060). Typical oxidizing reagents include pyridinium dichromate, chromium trioxide in pyridine, and dimethyl sulfoxide/oxalyl chloride (Swern oxidation). Compound V may in turn be reduced to VI by a number of methods set out in the literature (see J. March, Advanced Organic Chemistry, 3rd Ed., J. Wiley and Sons, New York, N.Y., 1985, pp. 809-814). Typical reducing reagents are sodium borohydride or lithium aluminum hydride. Thus, compounds V or VI can serve as intermediates in the synthesis of compounds of this invention.

SCHEME 6

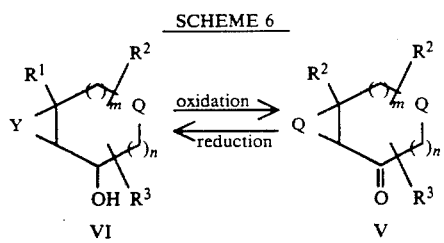

Compounds V and VI can be synthesized from VII and VIII respectively by standard methods of epoxidation (i.e., with perbenzoic acids, peracetic acids, basic hydrogen peroxide, basic t-butylperoxide, or aqueous N-bromosuccinimide followed by base) for Y=O and by standard methods of cyclopropanation (i.e., Simmons-Smith reaction, diazo insertion reaction, carbene insertion reaction, sulfur ylide transfer reagents; see J. March, *Advanced Organic Chemistry*, 3rd Ed., J. Wiley and Sons, New York, N.Y., 1985, pp. 768-774) for $Y=CR^6R^7$.

SCHEME 7

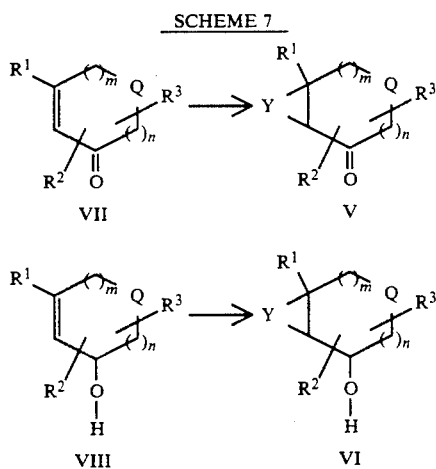

Alcohol VIII may be oxidized to VII and VII may be reduced to VIII as described previously for the interconversions of V and VI (vide supra).

SCHEME 8

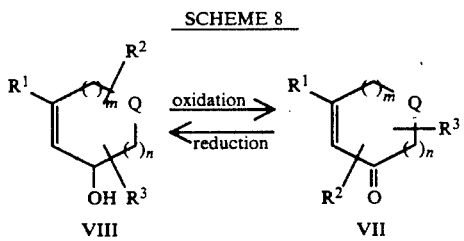

Compounds of Formulas VI and VIII in which the hydroxyl is positioned on a tertiary carbon may be synthesized by addition of an organometallic reagent $R^2M$ or $R^3M$ (when $R^2$ and $R^3$ are $C_1-C_4$ alkyl or $C_1-C_4$ haloalkyl and in which M is typically lithium or a magnesium halide) to ketones V and VII, respectively.

Compounds of Formula VII are available by a number of methods set out in the literature. For example, compounds of Formula VII can be prepared by reaction of compounds of Formula IX with an organometallic reagent $R^1M$ in an ethereal solvent such as tetrahydrofuran or diethyl ether. Compounds of Formula IX are generally known in the literature.

SCHEME 9

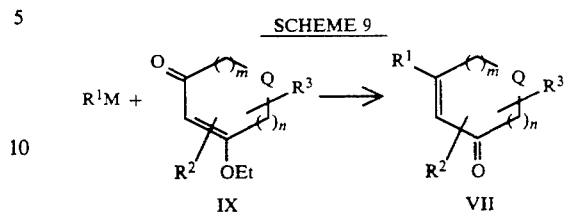

Alternatively, compounds of Formula VII may be prepared by reaction of compounds of Formula X with an organometallic reagent $R^1M$ in an ethereal solvent such as tetrahydrofuran or diethyl ether to form XI. Oxidation of XI with an oxidant such as $CrO_3/H_2SO_4$ in an ethereal solvent affords VII. Compounds of Formula X are generally known in the literature.

SCHEME 10

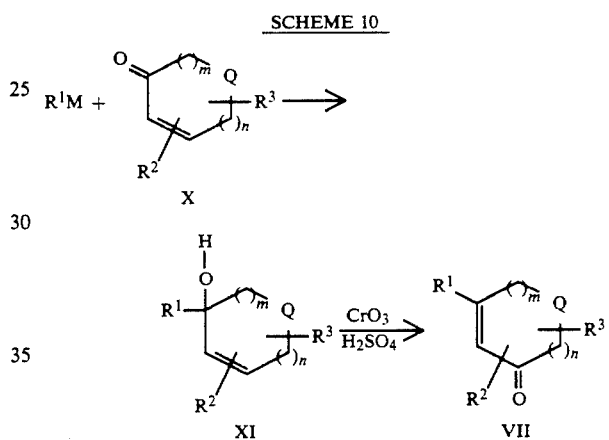

Those skilled in the art will recognize that Formula I compounds can contain two or more asymmetric carbon atoms. The stereoisomers that result can be separated using standard methods known in the art if desired.

EXAMPLES

Example 1

Synthesis of
1-[5-[4-(1,1-dimethylethyl)phenyl]-1-methyl-6-oxabicyclo[3.1.0]hexan-2-yl]-cis-3,5-dimethylpiperidine-[1α,2β,5α]

A solution of 25.7 g (0.12 mol) of 3-(4-t-butylphenyl)-2-methyl-2-cyclopenten-1-one (EP 0259977) dissolved in 40 mL of ether was cooled to 0° C. Added dropwise was 43.7 mL (43.7 mmol) of a solution of 1M lithium aluminum hydride in THF. After stirring 20 min, the mixture was quenched by dropwise addition of saturated aqueous $NaHSO_3$. The mixture was dried ($MgSO_4$), solids were filtered and the filtrate was stripped to afford 26.8 g of 1-(4-t-butylphenyl)-2-methyl-cyclopenten-3-ol as an oil which slowly solidified.

A solution of 23.6 g (0.10 mol) of 1-(4-t-butylphenyl)-2-methyl-cyclopenten-3-ol was dissolved in 20 mL of $CH_2Cl_2$ and cooled in an ice-water bath. Saturated aqueous $Na_2CO_3$ (50 mL) was added. 19.4 g (0.11 mol) of 80% m-chloroperbenzoic acid was added and the mixture was stirred 30 min. 50 mL of saturated aqueous NaHSO₃ was added as was 100 mL more saturated aqueous Na₂CO₃. The mixture was extracted twice with CH₂Cl₂ which was in turn washed with water and brine. Drying (MgSO₄) and removal of solvent afforded 24.5 g of 5-(4-t-butyl-phenyl)-1-methyl-6-oxabicyclo[3.1.0]hexan-2-ol[1α,2β,5α] as an oil which slowly solidified.

A solution of 23.8 g of 5-[4-t-butylphenyl)-1-methyl-6-oxabicyclo[3.1.0]hexan-2-ol[1α,2β,5α] in 100 mL CH₂Cl₂ was added dropwise to a suspension of 54.6 (0.145 mol) pyridinium dichromate and 7.5 g (39 mmol) of pyridinium trifluoroacetate in 150 mL CH₂Cl₂ at room temperature. The mixture was stirred two days before being poured into 1 L of ether. The ether solution was filtered through a silica gel pad which was subsequently washed with additional ether. The filtrate was stripped and the residue was chromatographed on silica gel with 9:1 hexanes/ether to afford 13.8 g of 5-(4-t-butylphenyl)-1-methyl-6-oxabicyclo[3.1.0]hexan-2-one as an oil that slowly solidified.

A solution of 2.66 g (10.8 mmol) of 5-(4-t-butylphenyl)-1-methyl-6-oxabicyclo[3.1.0]hexan-2-one, 5.0 g (44 mmol) of cis-dimethylpiperidine, 5.8 g (44 mmol) of cis-dimethylpiperidine hydrochloride, 0.34 g (5.5 mmol) of sodium cyanoborohydride and 1.5 g of 4 Å powdered, activated molecular sieves in 20 mL of methanol was stirred at room temperature for 2 days. The mixture was diluted with ethyl acetate and washed with saturated, aqueous Na₂CO₃, water and brine. Drying (MgSO₄) and removal of solvent gave an oil which was chromatographed on silica gel with 20:1 hexanes/ethyl acetate followed with 4:1 hexanes/ethyl acetate to elute 1-[5-[4-(1,1-dimethylethyl)phenyl]-1-methyl-6-oxabicyclo[3.1.0]hexan-2-yl-cis-3,5-dimethylpiperidine[-1α,2β,5α].

EXAMPLE 2

Synthesis of 1-[5-[4-(1,1-dimethylethyl)phenyl]-1-methyl-6-oxabicyclo[3.1.0]hexan-2-yl]-piperidine-[1α,2α,5α]hydrochloride Trifluoroacetic anhydride (0.4 mL, 2.3 mmol) was added dropwise to a solution of 0.51 g (2.1 mmol) of 5-(4-t-butylphenyl)-1-methyl-6-oxabicyclo[3.1.0]-hexan-2-ol[1α,2α,5α] in 20 mL of pyridine at −5° C. The mixture was warmed to room temperature and stirred 1 hour before stripping off solvent. The residue was diluted with ethyl acetate and washed with 1N HCl, water and brine. Drying (MgSO₄) and removal of solvent gave 510 mg of 1-[5-[4-(1,1-dimethylethyl)phenyl]-1-methyl-6-oxabicyclo[3.1.0]-hexan-2-yl]pyridinium[1α,2β,5α] chloride as an off white solid.

A solution of 0.4 g (1.2 mmol) of 1-[5-[4-(1,1-dimethylethyl)phenyl]-1-methyl-6-oxabicyclo[3.1.0]-hexan-2-yl]-pyridinium[1α,2β,5α] chloride, 0.4 g of 5% rhodium on alumina and 0.16 g (1.2 mmol) K₂CO₃ in 50 mL of ethanol was hydrogenated at 1 atm. pressure for 17 hours at room temperature. The reaction mixture was filtered through a Celite ® pad and rinsed through with ethyl acetate. Solvent was stripped and the residue was dissolved in ether. Some insoluble particulate matter was filtered off and solvent was stripped to afford an oil. The oil was dissolved in ether. An ethereal solution of 1N HCl was added and 0.21 g of 1-[5-[4-(1,1-dimethylethyl)phenyl]-1-methyl-6-oxabicyclo[3.1.0]hexan-2-yl]-piperidine[1α,2β,5α] hydrochloride precipitated as a white solid.

Examples of compounds of the invention are shown in Tables 1-2. Variables correspond to compounds of Formula I. Abbreviations are as follows:

t-Bu is tertiary butyl
i-Pr is isopropyl
Me is methyl
Et is phenyl
Ph is Phenyl
n-Bu is normal butyl
Bnz is benzyl
Me-O is methoxy
CN is cyano
Et-O is ethoxy
HO is hydroxy
TMS is trimethylsilyl.

TABLE 1

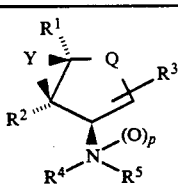

| R¹ | R² | R³ | (O)p<br>NR⁴R⁵ | Q | Y |
|---|---|---|---|---|---|
| 4-TMS—Ph | Me | H | cis-3,5-di-Me-piperidine | CH₂ | O |
| 4-TMS—Ph | Me | H | trans-3,5-di-Me-piperidine | CH₂ | O |
| 4-t-BuPh | Me | H | cis-3,5-di-Me-piperidine | CH₂ | O |
| 4-t-BuPh | Me | H | trans-3,5-di-Me-piperidine | CH₂ | O |
| 4-CF₃—BuPh | Me | H | trans-3,5-di-Me-piperidine | CH₂ | O |
| 4-t-BuPh | Me | H | 3-Me-piperidine | CH₂ | O |
| 4-TMS—BuPh | Me | H | 3-Me-piperidine | CH₂ | O |
| 4-t-BuPh | Me | H | pyrrolidine | CH₂ | O |
| 4-t-BuPh | Me | H | 3,3-di-Me-piperidine | CH₂ | O |
| 4-t-BuPh | Me | H | cis-3,5-di-Me-piperidine | CH₂ | O |
| 4-t-BuPh | Me | H | piperidine | CH₂ | O |
| 4-TMS—Ph | Me | H | piperidine | CH₂ | O |
| 4-t-BuPh | Me | H | cis-di-Me-morpholine | CH₂ | O |
| 4-t-BuPh | Me | 3-OMe | piperidine | CH₂ | O |
| 4-t-BuPh | Me | H | perhydro-iso-quinoline | CH₂ | O |
| 4-TMS—BuPh | Me | H | perhydro-iso-quinoline | CH₂ | O |

TABLE 1-continued

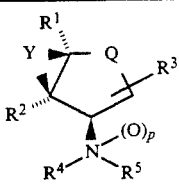

| R¹ | R² | R³ | (O)p<br>NR⁴R⁵ | Q | Y |
|---|---|---|---|---|---|
| 4-t-BuPh | Me | H | 4-(2-HO—Et)-piperidine | CH₂O | |
| 4-TMS—Ph | Me | H | 4-(2-HO—Et)-piperidine | CH₂O | |
| 4-i-PrPh | Me | H | 4-(2-HO—Et)-piperidine | CH₂O | |
| 4-t-BuPh | Me | H | di-Et-amine(trans R¹/N) | CH₂O | |
| 4-t-BuPh | Me | H | di-Et-amine(cis R¹/N) | CH₂O | |
| 4-t-BuPh | Me | 3-OMe | pyrrolidine | CH₂O | |
| 4-t-BuPh | Me | H | 1,2,5,6-tetrahydro-pyridine | CH₂O | |
| 4-t-BuPh | Me | H | 3,5-di-Me-1,2,5,6-tetrahydropyridine | CH₂O | |
| 4-t-BuPh | Me | H | 4-Ph-piperidine | CH₂O | |
| 4-t-BuPh | Me | H | 4-Ph-piperidine | CH₂O | |
| 4-t-BuPh | Me | H | 4-HO-pyrazine | CH₂O | |
| 4-t-BuPh | Me | H | 4-HO-pyrazine | CH₂O | |
| 4-t-BuPh | Me | H | 4-Me—O-pyrazine | CH₂O | |
| 4-t-BuPh | Me | H | 4-Me—O-pyrazine | CH₂O | |
| 4-t-BuPh | Me | H | 4-Me-pyrazine | CH₂O | |
| 4-t-BuPh | Me | H | 4-i-Pr-pyrazine | CH₂O | |
| 4-t-BuPh | Me | H | 3-CN-piperidine | CH₂O | |
| 4-t-BuPh | Me | H | 6-HO-4,4,8α-tri-Me-perhydro-iso-quinoline | CH₂O | |
| 4-t-BuPh | Me | H | 6-HO-4,8α,-di-Me-perhydro-iso-quinoline | CH₂O | |
| 4-t-BuPh | Me | H | 4-CN-piperidine | CH₂O | |
| 4-t-BuPh | Me | H | 4-(4-Cl—Ph)-piperidine | CH₂O | |
| 4-t-BuPh | Me | H | 4-Et—O-piperidine | CH₂O | |
| 4-t-BuPh | Me | H | 4-n-Bu-piperidine | CH₂O | |
| 4-t-BuPh | Me | H | 4-(2-HO-2-Me—Pr)-piperidine | CH₂O | |
| 4-t-BuPh | Me | H | 2,6-di-Me-piperidine | CH₂O | |
| 4-t-BuPh | Me | H | 4-CN-5-Me-1,2,5,6-tetrahydropyridine | CH₂O | |
| 4-t-BuPh | Me | H | 3,5-di-Me-morpholine | CH₂CH₂ | |
| 4-t-BuPh | Me | 3-OMe | 3,5-di-Me-morpholine | CH₂CH₂ | |
| 4-i-PrPh | Me | H | 3,5-di-Me-morpholine | CH₂CH₂ | |
| 5-Me-2-heptyl | Me | H | 3,5-di-Me-morpholine | CH₂CH₂ | |
| 5-Me-hexyl | Me | H | 3,5-di-Me-morpholine | CH₂CH₂ | |
| 5-Me-2-heptenyl | Me | H | 3,5-di-Me-morpholine | CH₂CH₂ | |
| cyclohexyl | Me | H | 3,5-di-Me-morpholine | CH₂CH₂ | |
| 4-t-BuPh | H | H | 3,5-di-Me-morpholine | CH₂CH₂ | |
| 4-i-PrPh | H | H | 3,5-di-Me-morpholine | CH₂CH₂ | |
| 5-Me-2-heptyl | H | H | 3,5-di-Me-morpholine | CH₂CH₂ | |
| 5-Me-hexyl | H | H | 3,5-di-Me-piperidine | CH₂CH₂ | |
| 6-Me-2-heptenyl | H | H | 3,5-di-Me-piperidine | CH₂CH₂ | |
| cyclohexyl | H | H | 3,5-di-Me-piperidine | CH₂CH₂ | |
| 4-t-BuPh | CN | H | 3,5-di-Me-piperidine | CH₂CH₂ | |
| 4-i-PrPh | CN | H | 3,5-di-Me-piperidine | CH₂CH₂ | |
| 4-t-BuPh | Me | H | 3-Me-piperidine | CH₂CH₂ | |
| 4-t-BuPh | Me | H | trans-perhydro-iso-quinoline | CH₂CH₂ | |
| 4-t-BuPh | Me | H | piperidine | CH₂CH₂ | |
| 4-t-BuPh | Me | H | 4-(2-HO—Et)-piperidine | CH₂CH₂ | |
| 4-t-BuPh | Me | H | di-Et-amine | CH₂CH₂ | |
| 4-t-BuPh | Me | H | 1,2,5,6-tetrahydro-pyridine | CH₂CH₂ | |
| 4-t-BuPh | Me | H | 3,5-di-Me-1,2,5,6-tetrahydro-pyridine | CH₂CH₂ | |
| 4-t-BuPh | Me | H | 4-Ph-piperdine | CH₂CH₂ | |
| 4-t-BuPh | Me | H | 6-HO-4,8α-di-Me-perhydro-iso-quinoline | CH₂CH₂ | |
| 4-t-BuPh | Me | H | 4-CN-piperidine | CH₂CH₂ | |
| 4-t-BuPh | Me | H | 3-CN-piperidine | CH₂CH₂ | |
| 4-t-BuPh | Me | H | 6-HO-4,4,8α-tri-Me-perhydro-iso-quinoline | CH₂CH₂ | |
| 4-t-BuPh | Me | H | 3,5-di-Me-piperidine | O | CF₂ |
| 4-t-BuPh | Me | H | 3,5-di-Me-piperidine | CH₂CCl₂ | |
| 4-t-BuPh | Me | H | 3,5-di-Me-piperidine | O | C(CH₃)₂ |
| 4-t-BuPh | Me | H | 3,5-di-Me-piperidine | CH₂CHCN | |
| 4-t-BuPh | Me | H | 3,5-di-Me-piperidine | O | CCN₂ |
| 4-t-BuPh | Me | H | 3,5-di-Me-piperidine | CH₂C(CH₃)CN | |
| 4-t-BuPh | Me | H | 3,5-di-Me-piperidine | O | CHCF₃ |
| 4-t-BuPh | Me | H | 3,5-di-Me-piperidine | CH₂CHCl | |
| 4-i-PrPh | Me | H | 3,5-di-Me-piperidine | CH₂CHOMe | |
| 4-i-BuPh | Me | H | 3,5-di-Me-piperidine | CH₂O | |
| 4-t-Bu-cyclohexyl | Me | H | 3,5-di-Me-piperidine | CH₂O | |

TABLE 1-continued

| R¹ | R² | R³ | NR⁴R⁵ (O)$_p$ | Q | Y |
|---|---|---|---|---|---|
| 6-Me-2-heptyl | Me | H | 3,5-di-Me-piperidine | CH₂O | |
| 5-Me-2-heptenyl | Me | H | 3,5-di-Me-piperidine | CH₂O | |
| 5-Me-hexyl | Me | H | 3,5-di-Me-piperidine | CH₂O | |
| 4-t-Bu-benzyl | Me | H | 3,5-di-Me-piperidine | CH₂O | |
| 4-i-PrPh | H | 2-CH₃ | 3,5-di-Me-morpholine | CH₂CH₂ | |
| 4-i-PrPh | H | 4-CH₃ | 3,5-di-Me-morpholine | CH₂CH₂ | |
| 4-i-PrPh | H | 3-CH₃ | 3,5-di-Me-morpholine | CH₂CH₂ | |
| 4-t-BuPh | H | 3-OCH₃ | piperidine | CH₂CH₂ | |
| 4-t-BuPh | H | 4-Cl | piperidine | CH₂CH₂ | |
| 4-t-BuPh | H | 4-F | piperidine | CH₂CH₂ | |
| 4-t-BuPh | H | 4-CF₃ | piperidine | CH₂CH₂ | |
| 4-t-BuPh | H | 3-CF₃ | piperidine | CH₂CH₂ | |
| 4-t-BuPh | C₂H₅ | H | piperidine | CH₂CH₂ | |
| 4-t-BuPh | OC₂H₅ | H | piperidine | CH₂CH₂ | |
| 4-t-BuPh | CF₃ | H | 3,5-di-Me-piperidine | CH₂O | |
| 4-t-BuPh | CH₂F | H | 3,5-di-Me-piperidine | CH₂O | |
| 4-t-BuPh | CH₂Cl | H | 3,5-di-Me-piperidine | CH₂O | |
| 4-t-BuPh | CN | 4-CH₃ | piperidine | CH₂CH₂ | |
| 4-t-BuPh | CN | 3-CH₃ | piperidine | CH₂CH₂ | |
| 4-Cl-2-Me-benzyl | Me | H | 3,5-di-Me-morpholine | CH₂CH₂ | |
| 4-t-Bu-2-Me-benzyl | Me | H | 3,5-di-Me-morpholine | CH₂CH₂ | |
| 2,4-di-Cl-2-Me-benzyl | Me | H | 3,5-di-Me-morpholine | CH₂CH₂ | |
| 2,4-di-F-benzyl | Me | H | 3,5-di-Me-morpholine | CH₂CH₂ | |
| 4-t-Bu-2-CN-benzyl | Me | H | 3,4-di-Me-pyrrolidine | CH₂CH₂ | |
| 4-[NCC(Me)₂]-phenyl | Me | H | pyrrolidine | CH₂CH₂ | |
| 4-Me-1-pentynyl | Me | H | 3,5-di-Me-piperidine | CH₂O | |
| 2-Cl-4-t-BuPh | Me | H | 3,5-di-Me-piperidine | CH₂O | |
| 2-OMe-4-t-BuPh | Me | H | 3,5-di-Me-piperidine | CH₂O | |
| 2-F-4-i-Ph | Me | H | 3,5-di-Me-piperidine | CH₂O | |
| 4-CF₃—Ph | Me | H | 3,5-di-Me-piperidine | CH₂O | |
| 1-(4-t-BuPh)-ethenyl | Me | H | 3,5-di-Me-piperidine | CH₂O | |
| 1-(4-t-BuPh)-ethenyl | Me | H | piperidine | CH₂O | |
| 1-(4-t-BuPh)-ethenyl | Me | H | 3,5-di-Me-morpholine | CH₂CH₂ | |
| 1-(4-t-BuPh)-ethenyl | Me | H | morpholine | CH₂CH₂ | |
| 4-n-BuPh | H | H | piperidine | O | CH₂ |
| 4-t-Bu-cyclohexyl | H | H | piperidine | O | CH₂ |
| n-Bu | H | H | piperidine | O | CF₂ |
| cyclopentyl | H | H | piperidine | O | CCl₂ |
| 6-Me-hexyl | H | H | piperidine | S | CH₂ |
| 4-i-Pr-Ph | H | H | piperidine | S | CH₂ |
| 4-t-BuPh | Me | H | 3,5-di-Me-piperidine (N-oxide) | CH₂O | |
| 4-t-BuPh | Me | H | 3,5-di-Me-piperidine (N-oxide) | CH₂CH₂ | |
| 4-t-BuPh | Me | H | piperidine(N-oxide) | CH₂O | |
| 4-t-BuPh | Me | H | piperidine(N-oxide) | CH₂CH₂ | |
| 4-t-BuPh | Me | H | 3,5-di-Me-morpholine (N-oxide) | CH₂O | |
| 4-t-BuPh | Me | H | 3,5-di-Me-morpholine (N-oxide) | CH₂CH2 | |
| 4-t-BuPh | Me | H | perhydro-iso-quinoline (N-oxide) | CH₂CH₂ | |

TABLE 2

| R¹ | R² | R³ | Y | NR⁴R⁵ (O)$_p$ | Q¹ | Q² |
|---|---|---|---|---|---|---|
| 4-i-Pr-Ph | Me | H | O | morpholine | CH₂ | CH₂ |

TABLE 2-continued $$\begin{array}{c} R^1 \quad Q^1-Q_2 \\ Y \\ R^2 \\ R^4-N-(O)_p \\ \phantom{R^4-N-}R^5 \end{array}$$

| $R^1$ | $R^2$ | $R^3$ | Y | $\underset{NR^4R^5}{(O)_p}$ | $Q^1$ | $Q^2$ |
| --- | --- | --- | --- | --- | --- | --- |
| 4-t-BuPh | Me | H | O | 3,5-di-Me-morpholine | $CH_2$ | $CH_2$ |
| 2,4-di-Cl—Bnz | Me | H | $CH_2$ | 3,5-di-Me-morpholine | $CH_2$ | $CH_2$ |
| n-pentyl | Me | H | O | piperidine | $CH_2$ | $CH_2$ |
| 1-CN-5-Me-1-hexyl | Me | H | $CH_2$ | morpholine | $CH_2$ | $CH_2$ |
| 4-t-BuPh | H | H | O | 3,5-di-Me-morpholine | $CH_2$ | $CH_2$ |
| 4-t-BuPh | Me | H | O | 3-piperidine | $CH_2$ | $CH_2$ |
| 4-i-PrPh | CN | H | $CH_2$ | pyrrolidine | $CH_2$ | $CH_2$ |
| 4-Et—Ph | $CF_3$ | H | $CH_2$ | 2-Me-pyrrolidine | $CH_2$ | $CH_2$ |
| 4-i-PrPh | i-Pr | H | O | 2,5-di-Me-pyrrolidine | $CH_2$ | $CH_2$ |
| 4-t-BuPh | H | 3-Me | O | 3,5-di-Me-piperidine | $CH_2$ | $CH_2$ |
| 4-t-Bu—Ph | H | 5-F | $CH_2$ | 3,5-di-Me-1,2,4,5-tetrahydro-pyridine | $CH_2$ | $CH_2$ |
| 4-t-BuPh | H | H | $CCl_2$ | 4-Me—O-piperazine | $CH_2$ | $CH_2$ |
| 4-t-BuPh | H | H | $CF_2$ | perhydro-iso-quinoline | $CH_2$ | $CH_2$ |
| 4-t-BuPh | H | H | $C(CH_3)_2$ | 3-Me-morpholine | $CH_2$ | $CH_2$ |
| 4-t-BuPh | H | H | CHCN | 3,5-di-Me-morpholine | $CH_2$ | $CH_2$ |
| 4-t-BuPh | H | H | CH(i-Pr) | 3,5-di-Me-morpholine | $CH_2$ | $CH_2$ |
| 4-t-BuPh | H | H | $CH_2$ | piperidine | O | $CH_2$ |
| 4-t-BuPh | H | H | O | 3,5-di-Me-piperidine | $CH_2$ | O |
| 4-t-BuPh | H | H | $CH_2$ | 3,5-di-Me-piperidine | $CH_2$ | S |
| 4-t-BuPh | Me | H | O | 3,5-di-Me-piperidine (N-oxide) | $CH_2$ | $CH_2$ |
| 4-t-BuPh | Me | H | $CH_2$ | 3,5-di-Me-piperidine (N-oxide) | $CH_2$ | CH2 |
| 4-t-BuPh | Me | H | O | piperidine(N-oxide) | $CH_2$ | $CH_2$ |
| 4-t-BuPh | Me | H | $CH_2$ | piperidine(N-oxide) | $CH_2$ | $CH_2$ |
| 4-t-BuPh | Me | H | O | 3,5-di-Me-morpholine (N-oxide) | $CH_2$ | $CH_2$ |
| 4-t-BuPh | Me | H | $CH_2$ | 3,5-di-Me-morpholine (N-oxide) | $CH_2$ | $CH_2$ |
| 4-t-BuPh | Me | H | O | 3,5-di-Me-piperidine (N-oxide) | O | $CH_2$ |
| 4-t-BuPh | Me | H | $CH_2$ | 3,5-di-Me-piperidine (N-oxide) | O | $CH_2$ |
| 4-t-BuPh | Me | H | O | piperidine(N-oxide) | O | $CH_2$ |
| 4-t-BuPh | Me | H | $CH_2$ | piperidine(N-oxide) | O | $CH_2$ |
| 4-t-BuPh | Me | H | O | 3,5-di-Me-piperidine (N-oxide) | $CH_2$ | O |
| 4-t-BuPh | Me | H | $CH_2$ | 3,5-di-Me-piperidine (N-oxide) | $CH_2$ | O |
| 4-t-BuPh | Me | H | O | 3-Me-piperidine (N-oxide) | $CH_2$ | O |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactants, and (b) about 1% to 99.9% solid or liquid inert diluent(s). More specifically, they will contain these ingredients in the following approximate proportions:

| | Weight Percent* | | |
| --- | --- | --- | --- |
| | Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredients plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff and "Perry's Chemical Engineer's Handbook", 5th Ed., McGraw-Hill, New York, 1973, pp. 8–59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated. One skilled in the art will recognize that Examples A, B, C, E, I, K, L and M are inappropriate wherein the active ingredient is an oil.

Example A

Wettable Powder

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 80% |
| sodium alkylnaphthalenesulfonate | 2% |
| sodium liginsulfonate | 2% |
| synthetic amorphous silica | 3% |
| kaolinite | 13% |

The ingredients are blended, hammer-milled until all the solid are essentially under 50 microns, reblended, and packaged.

Example B

Wettable Powder

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

Example C

Granule

| | |
|---|---|
| Wettable Powder of Example A | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

Example D

Extruded Pellet

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 25% |
| anhydrous sodium sulfate | 10% |
| crude calcium liginsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Example E

Oil Suspension

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspensions may be applied directly, but preferably after being extended with oils or emulsified in water.

Example F

Wettable Powder

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 20% |
| sodium alkylnaphthalenesulfonate | 4% |
| sodium liginsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Example G

Low Strength Granule

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 1% |
| N,N-dimethylformamide | 9% |
| attapulgite granule (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

Example H

Aqueous Suspension

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 10% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 86.7% |

The ingredients are blended and ground together in a sand mill to produce particles essentially all under 5 microns in size.

Example I

Solution

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α], HCl salt | 5% |
| water | 95% |

The salt is added directly to the water with stirring to produce the solution, which may then be Packaged for use.

Example J

Low Strength Granule

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 0.1% |
| attapulgite granules (U.S.S. 20-40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

Example K

Granule

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

Example L

High Strength Concentrate

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

Example M

Wettable Powder

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 90% |
| dioctyl sodium sulfosuccinate | 0.1% |
| synthetic fine silica | 9.9% |

The ingredients are blended and ground in a hammer-mill to produce particles essentially all below 100 mi-

Example N

Wettable Powder

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

Example O

Oil Suspension

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 35% |
| blend of polyalcohol carboxylic esters and oil-soluble petroleum sulfonates | 6% |
| xylene | 59% |

The ingredients are combined and stirred together in a sand mill to produce a solution. The product can be extended with oils, or emulsified in water.

Example P

Dust

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

Example Q

Emulsifiable Concentrate

| | |
|---|---|
| 1-[5-[4-(1,1-dimethylethyl)phenyl]-1-methyl-6-oxabicyclo[3.1.0]hexan-2-yl]-cis-3,5-dimethylpiperidine, [1α,2β,5α] | 20% |
| chlorobenzene | 74% |
| sorbitan monostearate and polyoxyethylene condensates thereof | 6% |

The ingredients are combined and stirred to produce a solution which can be emulsified in water for application.

Utility

The compounds of this invention are useful as plant disease control agents. They provide control of diseases caused by a broad spectrum of fungal plant pathogens in the *Basidiomycete*, *Ascomycete* and *Oomycete* classes. They are effective in controlling a broad spectrum of plant diseases, particularly foliar pathogens of ornamental, vegetable, field, cereal, and fruit crops. These pathogens include, *Erysiphe graminis*, *Uncinula necatur*, *Plasmopara viticola*, *Phytophthora infestans*, *Cerosporidium personatum*, *Cercospora arachidicola*, *Cercospora beticola*, *Botrytis cinerea*, *Podosphaera leucotricha*, *Venturia inaequalis*, *Puccinia recondita*, *Puccinia graminis*, *Hemileia vastatrix*, *Puccinia striiformis*, *Puccinia arachidis*, and other species closely related to these pathogens. They also control seed pathogens.

The compounds of this invention can be mixed with fungicides, bactericides, acaricides, nematicides, insecticides or other biologically active compounds in order to achieve desired results with a minimum of expenditure of time, effort and material. Suitable agents of this type are well-known to those skilled in the art. Some are listed below:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalamide (captan)
N-trichloromethylthiophthalimide (folpet)
dimethyl 4,4'-(o-phenylene)bis(3-thioallophanate) (thiophanate-methyl)
2-(thiazol-4-yl)benzimidazole (thiabendazole)
aluminum tris(O-ethyl phosphonate)(phosethyl aluminum)
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[1,1,2,2-tetrachloroethyl)thio]cyclohex-4-ene-1,2-dicarbioximide (captafol)
3-(3,5-dichlorophenyl)-N-(1-methylethyl)-2,4-dioxo-1-imidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate (edifenphos)
4-(3-(4-(1,1-dimethyl-ethyl)phenyl)-2-methyl)propyl-2,6-dimethylmorpholine (fenpropimorph)
4-(3-4(1,1-dimethyl-ethyl)phenyl)-2-methyl)propyl-piperidine (fenpropidine)
1-(4-chlorophenoxy)-3,3-dimethyl-1-1H-1,2,4-triazol-1-yl)butanone (triadimefon)
2-(4-chlorophenyl)-2-(1H-1,2,4-triazol-1-ylmethyl)-hexanenitrile (myclobutanil)
α-[2-(4-chlorophenyl)ethyl]-α-(1,1-dimethylethyl)-1H-1,2,4-triazole-1-ethanol (tebuconazol)
3-chloro-4-[4-methyl-2-(1H-1,2,4-triazol)-1-ylmethyl)-1,3-dioxolan-2-yl]phenyl-4-chlorophenyl ether (difenoconazole)
1-[2-(2,4-dichlorophenyl)pentyl]1H-1,2,4-triazole (penconazole)
(RS)-2,4'-difluoro-a-(1H-1,2,4-triazole-1-ylmethyl)-benzhydryl alcohol (flutriafol)
1-[[bis(4-fluorophenyl)methylsilyl)methyl]-1H-1,2,4-triazole (flusilazol)
N-propyl-N-[2-(2,4,6-trichlorophenoxy)ethyl]imidazole-1-carboxamide (prochloraz)

(±)-1-[2-(2,4-dichlorophenyl)-4-propyl-1,3-dioxolan-2-ylmethyl]-1H-1,2,4-triazole (propiconazole)
α-(2-chlorophenyl)-α-(4-chlorophenyl)-5-pyrimidinemethanol (fenarimol)
1-(4-Chlorophenoxy)-3,3-dimethyl-1-(1H-1,2,4-triazole-1-yl)butan-2-ol (triadimenol)
(2RS,3RS)-1-(2,4-dichlorophenyl)-4,4-dimethyl-2-(1H-1,2,4-triazol-1-yl)pentan-3-ol (diclobutrazol)
copper oxychloride
methyl N-(2,6-dimethylphenyl)-N-(2-furanylcarbonyl)-DL-alaninate (furalaxyl)

Bactericides tribasic copper sulfate
streptomycin sulfate
oxytetracycline

Acaricides senecioic acid, ester with 2-sec-butyl-4,6-dinitro-phenol (binapacryl)
6-methyl-1,3-dithiolo[2,3-B]quinonolin-2-one (oxythioquinox)
2,2,2-trichloro-1,1-bis(4-chlorophenyl)ethanol (dicofol)
bis(pentachloro-2,4-cyclopentadien-1-yl)(dienochlor)
tricyclohexyltin hydroxide (cyhexatin)
hexakis(2-methyl-2-phenylpropyl)distannoxane (fenbutatin oxide)

Nematicides

2-[diethoxyphosphinylimino]-1,3-diethietane (fosthietan)
S-methyl-1-(dimethylcarbamoyl)-N-(methylcarbamoyloxy)-thioformimidate (oxamyl)
S-methyl-1-carbamoyl-N-(methylcarbamoyloxy)thioformimidate
N-isopropylphosphoramidic acid, O-ethyl-O'-[4-(methylthio)-m-tolyl]diester (fenamiphos)

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-a-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl N-[[(methylamino)carbonyl]oxy]ethanimidothioate (methomyl)
N'-(4-chloro-o-tolyl)-N,N-dimethylformamidine (chlordimeform)
O,O-diethyl-O-(2-isopropyl-4-methyl-6-pyrimidyl)-phosphorothioate (diazinon)
octachlorocamphene (toxaphene)
O-ethyl O-p-nitrophenyl phenylphosphonothioate (EPN)
cyano(3-phenoxyphenyl)-methyl 4-chloro-α-(1-methylethyl)benzeneacetate (fenvalerate)
(3-phenoxyphenyl)methyl (+)-cis,trans-3-(2,2-dichloroethenyl)-2,2-dimethylcyclopropanecarboxylate (permethrin)
dimethyl N,N'-[thiobis(N-methylimmo)carbonyloxy]]-bis[ethanimidothioate] (thiodicarb)
phosphorothiolothionic acid, O-ethyl-O-[4-(methylthio)phenyl]-S-n-propyl ester (sulprofos)
α-cyano-3-phenoxybenzyl 3-(2,2-dichlorovinyl)-2,2-dimethylcyclopropane carboxylate (cypermethrin)
cyano(3-phenoxyphenyl)methyl 4-(difluoromethoxy)-α-(methylethyl)benzeneacetate (flucythrinate)
O,O-diethyl-O-(3,5,6-trichloro-2-pyridyl)phosphorothioate (chlorpyrifos)
O,O-dimethyl-S-[(4-oxo-1,2,3-benzotriazin-3-(4H)-yl)-methyl]phosphorodithioate (azinphos-methyl)
5,6-dimethyl-2-dimethylamino-4-pyrimidinyl dimethyl carbamate (pirimicarb)
S-(N-formyl-N-methylcarbamoylmethyl)-O,O-dimethyl phosphorodithioate (formothion)
S-2-(ethylthioethyl)-O,O-dimethyl phosphiorothioate (demeton-S-methyl)
α-cyano-3-phenoxybenzyl cis-3-(2,2-dibromovinyl)-2,2-dimethylcyclopropane carboxylate (deltamethrin)
cyano(3-phenoxyphenyl)methyl ester of N-(2-chloro-4-trifluoromethylphenyl)alanine (fluvalinate)

Application

Disease control is ordinarily accomplished by applying an effective amount of the compound either preinfection or post-infection to the portion of the plant to be protected such as the roots, stems, foliage, fruit, seeds, tubers or bulbs, or to the media (soil or sand) in which the plants to be protected are growing. The compound may also be applied to the seed, to protect the seed and seedling.

Rates of application for these compounds can be influenced by many factors of the environment and should be determined under actual use conditions. Foliage can normally be protected when treated at a rate of from less than 1 g/ha to 5000 g/ha of active ingredient. Plants growing in soil treated at a concentration from 0.1 to about 20 kg/ha can be protected from disease. Seed and seedlings can normally be protected when seed is treated at a rate of from 0.1 to 10 g per kilogram of seed.

Test A

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on apple seedlings. The following day the seedlings were inoculated with a spore suspension of *Venturia inaequalis* (the causal agent of apple scab) and incubated in a saturated atmosphere at 20° C. for 24 h, and then moved to a growth chamber at 22° C. for 11 days, after which disease ratings were made.

Test B

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on peanut seedlings. The following day the seedlings were inoculated with a spore suspension of *Cercosporidium personatum* (the causal agent of peanut late leafspot) and incubated in a saturated atmosphere at 22° C. for 24 h, a high humidity atmosphere at 22° C. to 30° C. for 5 days, and then moved to a growth chamber at 29° C. for 6 days, after which disease ratings were made.

Test C

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on wheat seedlings. The following day the seedlings were inoculated with a spore dust of *Erysiphe graminis* f. sp. tritici, (the causal agent of wheat powdery mildew) and incubated in a growth chamber at 20° C. for 7 days, after which disease ratings were made.

Test D

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

Test E

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on tomato seedlings. The following day the seedlings were inoculated with a spore suspension of *Phytophthor infestans* (the causal agent of potato and tomato late blight) and incubated in a saturated atmosphere at 20° C. for 24 h, and then moved to a growth chamber at 20° C. for 5 days, after which disease ratings were made.

Test F

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 h, moved to a growth chamber at 20° C. for 6 days, and then incubated in a saturated atmosphere at 20° C. for 24 h, after which disease ratings were made.

Test G

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

Results for Test A to G are given in Table A. In the table, a rating of 100 indicates 100% disease control and a rating of 0 indicates no disease control (relative to the carrier sprayed controls). NT indicates that no test was performed.

INDEX TABLE A

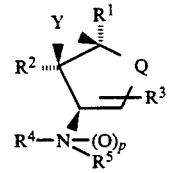

| CMPD NO. | $R^1$ | $R^2$ | $R^3$ | $\underset{R^5}{N-R^4}\overset{(O)_p}{|}$ | Q | Y | mp (°C.)[a] |
|---|---|---|---|---|---|---|---|
| 1 | 4-t-BuPh | Me | H | cis-3,5-di-Me-piperidine | $CH_2$ | O | 118–119 |
| 2 | 4-t-BuPh | Me | H | 3-Me-piperidine | $CH_2$ | O | 154–157 (HCl salt) |
| 3 | 4-t-BuPh | Me | H | piperidine | $CH_2$ | O | 124–128 |
| 4 | 4-t-BuPh | Me | H | cis-di-Me-morpholine | $CH_2$ | O | 158–161 |
| 5 | 4-t-BuPh | Me | H | perhydro-iso-quinoline | $CH_2$ | O | oil δ [1.2(s)] |
| 6 | 4-t-BuPh | Me | H | 4-(2-HO—Et)-piperidine | $CH_2$ | O | 96–99 |
| 7 | 4-t-BuPh | Me | H | di-Et-amine | $CH_2$ | O | 144–146 (HCl salt) |
| 8 | 4-t-BuPh | Me | H | pyrrolidine | $CH_2$ | O | 127–128 |
| 9 | 4-t-BuPh | Me | H | 4-Ph-piperidine | $CH_2$ | O | 128–132 |
| 10 | 4-t-BuPh | Me | H | 3,3-di-Me-piperidine | $CH_2$ | O | oil [0.45(s), 1.0(s), 1.2(s)] |
| 11 | 5-Me-hexyl | Me | H | cis-3,5-di-Me-piperidine | $CH_2$ | O | oil [3.0(t)] |
| 12 | 5-Me-hexyl | Me | H | cis-3,5-di-Me-morpholine | $CH_2$ | O | oil [3.0(t)] |

[a]NMR data, given for oil, is in ppm downfield from tetramethylsilane. Coupling are designated by (s)-singlet, (d)-doublet, (t)triplet, (q)-quartet.

TABLE A

| Cmpd No. | TEST A | TEST B | TEST C | TEST D | TEST E | TEST F | TEST G |
|---|---|---|---|---|---|---|---|
| 1 | 69 | 97 | 98 | 100 | 65 | 100 | 99 |
| 2 | 39 | 77 | 100 | NT | 26 | NT | 0 |
| 3 | 59 | 51 | 97 | 100 | 0 | NT | 0 |
| 4 | 98 | 66 | 98 | 83 | 0 | NT | 95 |
| 5 | 17 | 27 | 0 | NT | 25 | NT | 98 |
| 6 | 36 | 89 | 91 | 100 | 86 | NT | 83 |
| 7 | 88 | 56 | 94 | 18 | 26 | NT | 0 |
| 8 | 88 | 56 | 94 | 22 | 47 | NT | 0 |
| 9 | NT | NT | NT | NT | NT | NT | NT |
| 10 | NT | NT | NT | NT | NT | NT | NT |
| 11 | NT | NT | NT | NT | NT | NT | NT |
| 12 | NT | NT | NT | NT | NT | NT | NT |

What is claimed is:

1. A compound of the formula

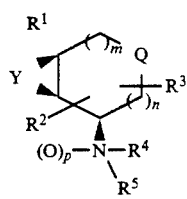

I wherein:
n is 1 or 2;
m is 0 or 1;
p is 0 or 1;
Q is C, O or S;
Y is O or $CR^6R^7$;
$R^1$ is $C_4$-$C_{10}$ alkyl, $C_4$-$C_{10}$ alkenyl, $C_4$-$C_{10}$ alkynyl, $C_4$-$C_{10}$ cyanoalkyl, $C_3$-$C_{10}$ cycloalkyl optionally substituted with $C_1$-$C_6$ alkyl, 2-thienyl substituted with $R^8$ and $R^9$, or $R^1$ is phenyl substituted with $R^8$ and $R^9$, or $R^1$ is styryl substituted with $R^8$ and $R^9$, or $R^1$ is

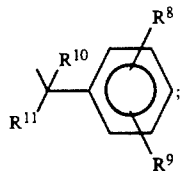

$R^2$, $R^3$, $R^{11}$, and $R^{12}$ are independently H, CN, halogen, $C_1$-$C_4$ alkyl, $C_1$-$C_4$ alkoxy or $C_1$-$C_4$ haloalkyl;
$R^4$ and $R^5$ are independently $C_1$-$C_6$ alkyl, phenethyl optionally substituted with 1-3 substituents selected from the group consisting of halogen, CN and $C_1$-$C_4$ alkyl, or $R^4$ and $R^5$ may be taken together with the nitrogen to which they are attached to form heterocycles of the formulas:

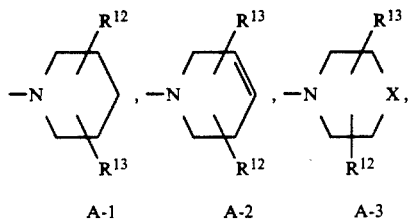

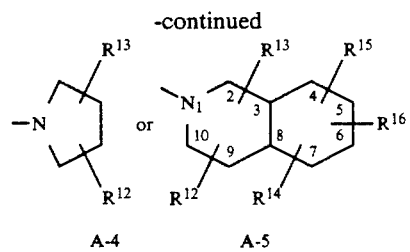

$R^6$ and $R^7$ are independently H, halogen, methyl, methoxy, CN or trifluoromethyl;
$R^8$ and $R^9$ are independently H, halogen, CN, $C_1$-$C_6$ alkyl, $C_1$-$C_6$ cyanoalkyl, $C_1$-$C_6$ haloalkyl, $C_3$-$C_6$ cycloalkyl, $C_3$-$C_6$ cycloalkylmethyl, $C_2$-$C_6$ alkenyl, $C_2$-$C_6$ alkynyl, $C_1$-$C_6$ alkoxy, phenyl optionally substituted with halogen, CN or $C_1$-$C_4$ alkyl, phenoxy optionally substituted with halogen, CN or $C_1$-$C_4$ alkyl, or silicon substituted with any three of the group consisting of $C_1$-$C_4$ alkyl, $C_2$-$C_4$ alkenyl, $C_2$-$C_4$ alkynyl and $C_1$-$C_3$ haloalkyl;
$R^{12}$ and $R^{13}$ are independently H, halogen, CN, $C_1$-$C_4$ alkyl, $C_2$-$C_4$ alkenyl, $C_1$-$C_4$ alkoxy, $C_1$-$C_4$ hydroxyalkyl or phenyl optionally substituted with 1-2 halogen;
$R^{14}$ and $R^{15}$ are independently H, halogen, CN, $C_1$-$C_4$ alkyl or $C_1$-$C_4$ alkoxy;
$R^{16}$ is H, OH, halogen, CN, $C_1$-$C_4$ alkyl or $C_1$-$C_4$ alkoxy;
X is O or $NR^{17}$;
$R^{17}$ is H, OH, $C_1$-$C_3$ alkyl or $C_1$-$C_3$ alkoxy;
Z is O or $CH_2$;
or an agriculturally suitable salt thereof provided that:
1) When m is 1, n is 1;
2) When m is 0 and Q is O or S, Y is $CR^6R^7$;
3) When $R^4$ and $R^5$ are taken together to form heterocycles of the Formula A-5, $R^{12}$ and $R^{13}$ may be substituted at positions 2, 3, 8, 9 or 10 and $R^{14}$, $R^{15}$ and $R^{16}$ may be substituted at positions 4, 5, 6 or 7;
4) When $R^2$ or $R^3$ are halogen or $C_1$-$C_4$ alkoxy, then they must not be substituted on a carbon atom attached to O, S or N;
5) $R^2$ or $R^3$ is CN, then they must not be substituted at the carbon atom attached to $NR^4R^5$.

2. A compound of claim 1 of the formula:

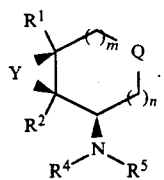

3. A compound of claim 2, wherein:
Y is O or $CH_2$;
$R^2$ is H, $CH_3$, $CH_2CH_3$ or CN;
$R^4$ and $R^5$ are taken together to form heterocycles of the formula A-1, A-2, A-3, A-4 or A-5;
$R^8$ and $R^9$ are independently H, halogen, CN, $C_1$–$C_6$ alkyl, $C_1$–$C_6$ cyanoalkyl, $C_1$–$C_6$ haloalkyl or $C_3$–$C_6$ cycloalkyl;
$R^{12}$ and $R^{13}$ are independently H, CN, $C_1$–$C_4$ alkyl, $C_1$–$C_4$ alkoxy or $C_1$–$C_4$ hydroxyalkyl;
$R^{14}$ and $R^{15}$ are independently H, CN or $CH_3$;
$R^{17}$ is H or OH; and
X is O.

4. A compound of claim 3 wherein:
m is 0;
n is 1; and
Q is $CH_2$.

5. A compound of claim 4 wherein:
$R^4$ and $R^5$ are taken together to form heterocycles of the structures A-1, A-3 or A-4.

6. A compound of claim 5 wherein:
$R^1$ is $C_4$–$C_{10}$ alkyl, $C_4$–$C_{10}$ cycloalkyl optionally substituted with $C_1$–$C_6$ alkyl, or $R^1$ is phenyl substituted with $R^8$, or $R^1$ is benzyl substituted with $R^8$ on the aryl moiety;
$R^2$ is H, $CH_3$ or CN;
$R^8$ is H, $C_1$–$C_6$ alkyl, $C_3$–$C_4$ cycloalkyl, CN or $CF_3$; and
$R^{13}$ and $R^{14}$ are independently H or $CH_3$.

7. A compound of claim 6 which is:
1-[5-[4-(1,1-dimethylethyl)phenyl]-1-methyl-6-oxabicyclo[3.1.0]hexan-2-yl]-cis-3,5-dimethylpiperidine, [1α,2β,5α].

8. An agriculturally suitable composition comprising a fungicidally effective amount of a compound of any of claims 1 to 6 or 7 and at least one of the following: surfactant, solid or liquid diluent.

9. A method for controlling fungus disease in plants which comprises applying to the locus to be protected an effective amount of a compound of any one of claims 1 to 6 or 7.

* * * * *

UNITED STATES PATENT AND TRADEMARK OFFICE
CERTIFICATE OF CORRECTION

PATENT NO. : 5,128,348

DATED : July 7, 1992

INVENTOR(S) : Gregory S. Basarab

It is certified that error appears in the above-identified patent and that said Letters Patent is hereby corrected as shown below:

In Column 2, line 10 through 16 should read:

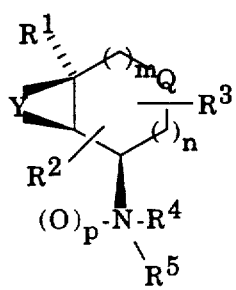

I

In Column 4, Scheme 1 should read:

SCHEME 1

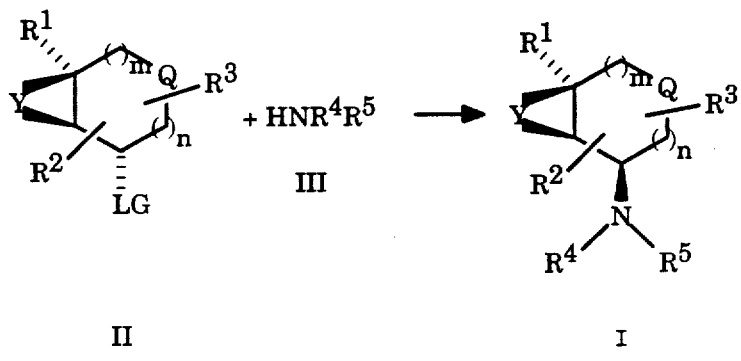

UNITED STATES PATENT AND TRADEMARK OFFICE
CERTIFICATE OF CORRECTION

PATENT NO. : 5,128,348

DATED : July 7, 1992

INVENTOR(S) : Gregory S. Basarab

Page 2 of 10

It is certified that error appears in the above-identified patent and that said Letters Patent is hereby corrected as shown below:

In Column 5, line 3: "pyridine V. The reaction is run neat with 1 to 100 equiv- " should read: --pyridine. The reaction is run neat with 1 to 100 equiv- --

In Column 5, line 4: "alents of V at temperatures between 25°C and 100°C." should read: --alents of a pyridine at temperatures between 25°C and 100°C.--In Column 5, Scheme 2 should read:

SCHEME 2

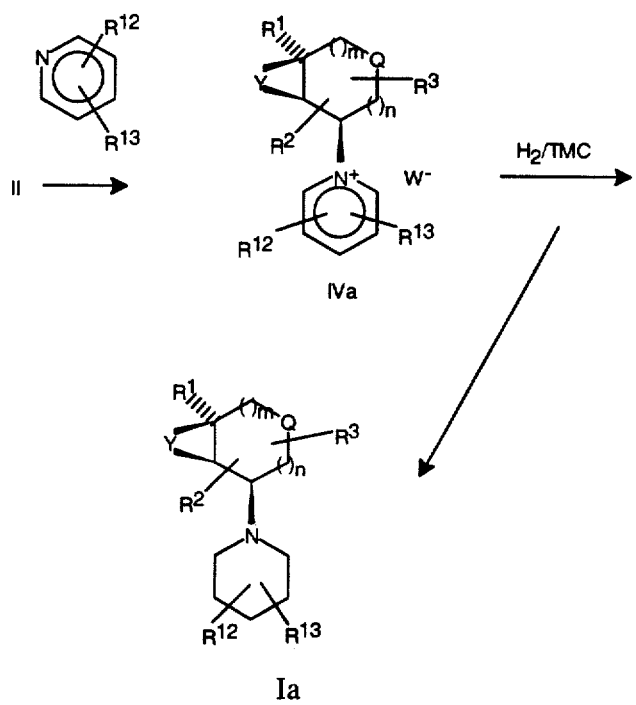

UNITED STATES PATENT AND TRADEMARK OFFICE
CERTIFICATE OF CORRECTION

PATENT NO. : 5,128,348

DATED : July 7, 1992

INVENTOR(S) : Gregory S. Basarab

It is certified that error appears in the above-identified patent and that said Letters Patent is hereby corrected as shown below:

In Columns 9 and 10 Table 1 should read:

TABLE 1

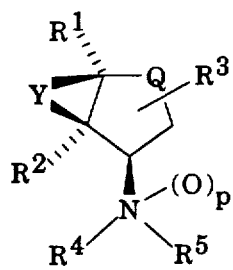

| $R^1$ | $R^2$ | $R^3$ | $\overset{(O)_p}{NR^4R^5}$ | Q | Y |
|---|---|---|---|---|---|
| 4-TMS-Ph | Me | H | cis-3,5-di-Me-piperidine | $CH_2$ | O |
| 4-TMS-Ph | Me | H | trans-3,5-di-Me-piperidine | $CH_2$ | O |
| 4-t-BuPh | Me | H | cis-3,5-di-Me-piperidine | $CH_2$ | O |
| 4-t-BuPh | Me | H | trans-3,5-di-Me-piperidine | $CH_2$ | O |
| 4-$CF_3$-BuPh | Me | H | trans-3,5-di-Me-piperidine | $CH_2$ | O |
| 4-t-BuPh | Me | H | 3-Me-piperidine | $CH_2$ | O |
| 4-TMS-BuPh | Me | H | 3-Me-piperidine | $CH_2$ | O |
| 4-t-BuPh | Me | H | pyrrolidine | $CH_2$ | O |

UNITED STATES PATENT AND TRADEMARK OFFICE
CERTIFICATE OF CORRECTION

PATENT NO. : 5,128,348
DATED : July 7, 1992
INVENTOR(S) : Gregory S. Basarab Page 4 of 10

It is certified that error appears in the above-identified patent and that said Letters Patent is hereby corrected as shown below:

| | | | | | |
|---|---|---|---|---|---|
| 4-t-BuPh | Me | H | 3,3-di-Me-piperidine | $CH_2$ | O |
| 4-t-BuPh | Me | H | cis-3,5-di-Me-piperidine | $CH_2$ | O |
| 4-t-BuPh | Me | H | piperidine | $CH_2$ | O |
| 4-TMS-Ph | Me | H | piperidine | $CH_2$ | O |
| 4-t-BuPh | Me | H | cis-di-Me-morpholine | $CH_2$ | O |
| 4-t-BuPh | Me | 3-OMe | piperidine | $CH_2$ | O |
| 4-t-BuPh | Me | H | perhydro-iso-quinoline | $CH_2$ | O |
| 4-TMS-BuPh | Me | H | perhydro-iso-quinoline | $CH_2$ | O |
| 4-t-BuPh | Me | H | 4-(2-HO-Et)-piperidine | $CH_2$ | O |
| 4-TMS-Ph | Me | H | 4-(2-HO-Et)-piperidine | $CH_2$ | O |
| 4-i-PrPh | Me | H | 4-(2-HO-Et)-piperidine | $CH_2$ | O |
| 4-t-BuPh | Me | H | di-Et-amine (trans $R^1$/N) | $CH_2$ | O |
| 4-t-BuPh | Me | H | di-Et-amine (cis $R^1$/N) | $CH_2$ | O |
| 4-t-BuPh | Me | 3-OMe | pyrrolidine | $CH_2$ | O |
| 4-t-BuPh | Me | H | 1,2,5,6-tetrahydropyridine | $CH_2$ | O |
| 4-t-BuPh | Me | H | 3,5-di-Me-1,2,5,6-tetrahydro-pyridine | $CH_2$ | O |
| 4-t-BuPh | Me | H | 4-Ph-piperidine | $CH_2$ | O |
| 4-t-BuPh | Me | H | 4-Ph-piperidine | $CH_2$ | O |
| 4-t-BuPh | Me | H | 4-HO-pyrazine | $CH_2$ | O |
| 4-t-BuPh | Me | H | 4-HO-pyrazine | $CH_2$ | O |
| 4-t-BuPh | Me | H | 4-Me-O-pyrazine | $CH_2$ | O |

UNITED STATES PATENT AND TRADEMARK OFFICE
CERTIFICATE OF CORRECTION

PATENT NO. : 5,128,348

DATED : July 7, 1992

INVENTOR(S) : Gregory S. Basarab

It is certified that error appears in the above-identified patent and that said Letters Patent is hereby corrected as shown below:

| | | | | | |
|---|---|---|---|---|---|
| 4-t-BuPh | Me | H | 4-Me-O-pyrazine | CH$_2$ | O |
| 4-t-BuPh | Me | H | 4-Me-pyrazine | CH$_2$ | O |
| 4-t-BuPh | Me | H | 4-i-Pr-pyrazine | CH$_2$ | O |
| 4-t-BuPh | Me | H | 3-CN-piperidine | CH$_2$ | O |
| 4-t-BuPh | Me | H | 6-HO-4,4,8α-tri-Me-perhydro-iso-quinoline | CH$_2$ | O |
| 4-t-BuPh | Me | H | 6-HO-4,8α-di-Me-perhydro-iso-quinoline | CH$_2$ | O |
| 4-t-BuPh | Me | H | 4-CN-piperidine | CH$_2$ | O |
| 4-t-BuPh | Me | H | 4-(4-Cl-Ph)-piperidine | CH$_2$ | O |
| 4-t-BuPh | Me | H | 4-Et-O-piperidine | CH$_2$ | O |
| 4-t-BuPh | Me | H | 4-n-Bu-piperidine | CH$_2$ | O |
| 4-t-BuPh | Me | H | 4-(2-HO-2-Me-Pr)-piperidine | CH$_2$ | O |
| 4-t-BuPh | Me | H | 2,6-di-Me-piperidine | CH$_2$ | O |
| 4-t-BuPh | Me | H | 4-CN-5-Me-1,2,5,6-tetra-hydropyridine | CH$_2$ | O |
| 4-t-BuPh | Me | H | 3,5-di-Me-morpholine | CH$_2$ | CH$_2$ |
| 4-t-BuPh | Me | 3-OMe | 3,5-di-Me-morpholine | CH$_2$ | CH$_2$ |
| 4-i-PrPh | Me | H | 3,5-di-Me-morpholine | CH$_2$ | CH$_2$ |
| 5-Me-2-heptyl | Me | H | 3,5-di-Me-morpholine | CH$_2$ | CH$_2$ |
| 5-Me-hexyl | Me | H | 3,5-di-Me-morpholine | CH$_2$ | CH$_2$ |
| 5-Me-2-heptenyl | Me | H | 3,5-di-Me-morpholine | CH$_2$ | CH$_2$ |
| cyclohexyl | Me | H | 3,5-di-Me-morpholine | CH$_2$ | CH$_2$ |

UNITED STATES PATENT AND TRADEMARK OFFICE
CERTIFICATE OF CORRECTION

PATENT NO. : 5,128,348
DATED : July 7, 1992
INVENTOR(S) : Gregory S. Basarab It is certified that error appears in the above-identified patent and that said Letters Patent is hereby corrected as shown below:

| | | | | | |
|---|---|---|---|---|---|
| 4-t-BuPh | H | H | 3,5-di-Me-morpholine | $CH_2$ | $CH_2$ |
| 4-i-PrPh | H | H | 3,5-di-Me-morpholine | $CH_2$ | $CH_2$ |
| 5-Me-2-heptyl | H | H | 3,5-di-Me-morpholine | $CH_2$ | $CH_2$ |
| 5-Me-hexyl | H | H | 3,5-di-Me-piperidine | $CH_2$ | $CH_2$ |
| 6-Me-2-heptenyl | H | H | 3,5-di-Me-piperidine | $CH_2$ | $CH_2$ |
| cyclohexyl | H | H | 3,5-di-Me-piperidine | $CH_2$ | $CH_2$ |
| 4-t-BuPh | CN | H | 3,5-di-Me-piperidine | $CH_2$ | $CH_2$ |
| 4-i-PrPh | CN | H | 3,5-di-Me-piperidine | $CH_2$ | $CH_2$ |
| 4-t-BuPh | Me | H | 3-Me-piperidine | $CH_2$ | $CH_2$ |
| 4-t-BuPh | Me | H | trans-perhydro-iso-quinoline | $CH_2$ | $CH_2$ |
| 4-t-BuPh | Me | H | piperidine | $CH_2$ | $CH_2$ |
| 4-t-BuPh | Me | H | 4-(2-HO-Et)-piperidine | $CH_2$ | $CH_2$ |
| 4-t-BuPh | Me | H | di-Et-amine | $CH_2$ | $CH_2$ |
| 4-t-BuPh | Me | H | 1,2,5,6-tetrahydro-pyridine | $CH_2$ | $CH_2$ |
| 4-t-BuPh | Me | H | 3,5-di-Me-1,2,5,6-tetrahydro-pyridine | $CH_2$ | $CH_2$ |
| 4-t-BuPh | Me | H | 4-Ph-piperidine | $CH_2$ | $CH_2$ |
| 4-t-BuPh | Me | H | 6-HO-4,8α-di-Me-perhydro-iso-quinoline | $CH_2$ | $CH_2$ |
| 4-t-BuPh | Me | H | 4-CN-piperidine | $CH_2$ | $CH_2$ |
| 4-t-BuPh | Me | H | 3-CN-piperidine | $CH_2$ | $CH_2$ |
| 4-t-BuPh | Me | H | 6-HO-4,4,8α-tri-Me-perhydro-iso-quinoline | $CH_2$ | $CH_2$ |

UNITED STATES PATENT AND TRADEMARK OFFICE
CERTIFICATE OF CORRECTION

PATENT NO. : 5,128,348

DATED : July 7, 1992

INVENTOR(S) : Gregory S. Basarab

It is certified that error appears in the above-identified patent and that said Letters Patent is hereby corrected as shown below:

| | | | | | |
|---|---|---|---|---|---|
| 4-t-BuPh | Me | H | 3,5-di-Me-piperidine | O | $CF_2$ |
| 4-t-BuPh | Me | H | 3,5-di-Me-piperidine | $CH_2$ | $CCl_2$ |
| 4-t-BuPh | Me | H | 3,5-di-Me-piperidine | O | $C(CH_3)_2$ |
| 4-t-BuPh | Me | H | 3,5-di-Me-piperidine | $CH_2$ | CHCN |
| 4-t-BuPh | Me | H | 3,5-di-Me-piperidine | O | $CCN_2$ |
| 4-t-BuPh | Me | H | 3,5-di-Me-piperidine | $CH_2$ | $C(CH_3)CN$ |
| 4-t-BuPh | Me | H | 3,5-di-Me-piperidine | O | $CHCF_3$ |
| 4-t-BuPh | Me | H | 3,5-di-Me-piperidine | $CH_2$ | CHCl |
| 4-t-PrPh | Me | H | 3,5-di-Me-piperidine | $CH_2$ | CHOMe |
| 4-i-BuPh | Me | H | 3,5-di-Me-piperidine | $CH_2$ | O |
| 4-t-Bu-cyclohexyl | Me | H | 3,5-di-Me-piperidine | $CH_2$ | O |
| 6-Me-2-heptyl | Me | H | 3,5-di-Me-piperidine | $CH_2$ | O |
| 5-Me-2-heptenyl | Me | H | 3,5-di-Me-piperidine | $CH_2$ | O |
| 5-Me-hexyl | Me | H | 3,5-di-Me-piperidine | $CH_2$ | O |
| 4-t-Bu-benzyl | Me | H | 3,5-di-Me-piperidine | $CH_2$ | O |
| 4-i-PrPh | H | 2-$CH_3$ | 3,5-di-Me-morpholine | $CH_2$ | $CH_2$ |
| 4-i-PrPh | H | 4-$CH_3$ | 3,5-di-Me-morpholine | $CH_2$ | $CH_2$ |
| 4-i-PrPh | H | 3-$CH_3$ | 3,5-di-Me-morpholine | $CH_2$ | $CH_2$ |
| 4-t-BuPh | H | 3-$OCH_3$ | piperidine | $CH_2$ | $CH_2$ |
| 4-t-BuPh | H | 4-Cl | piperidine | $CH_2$ | $CH_2$ |
| 4-t-BuPh | H | 4-F | piperidine | $CH_2$ | $CH_2$ |

UNITED STATES PATENT AND TRADEMARK OFFICE
CERTIFICATE OF CORRECTION

PATENT NO. : 5,128,348

DATED : July 7, 1992

INVENTOR(S) : Gregory S. Basarab

It is certified that error appears in the above-identified patent and that said Letters Patent is hereby corrected as shown below:

| | | | | | |
|---|---|---|---|---|---|
| 4-t-BuPh | H | 4-$CF_3$ | piperidine | $CH_2$ | $CH_2$ |
| 4-t-BuPh | H | 3-$CF_3$ | piperidine | $CH_2$ | $CH_2$ |
| 4-t-BuPh | $C_2H_5$ | H | piperidine | $CH_2$ | $CH_2$ |
| 4-t-BuPh | $OC_2H_5$ | H | piperidine | $CH_2$ | $CH_2$ |
| 4-t-BuPh | $CF_3$ | H | 3,5-di-Me-piperidine | $CH_2$ | O |
| 4-t-BuPh | $CH_2F$ | H | 3,5-di-Me-piperidine | $CH_2$ | O |
| 4-t-BuPh | $CH_2Cl$ | H | 3,5-di-Me-piperidine | $CH_2$ | O |
| 4-t-BuPh | CN | 4-$CH_3$ | piperidine | $CH_2$ | $CH_2$ |
| 4-t-BuPh | CN | 3-$CH_3$ | piperidine | $CH_2$ | $CH_2$ |
| 4-Cl-2-Me-benzyl | Me | H | 3,5-di-Me-morpholine | $CH_2$ | $CH_2$ |
| 4-t-Bu-2-Me-benzyl | Me | H | 3,5-di-Me-morpholine | $CH_2$ | $CH_2$ |
| 2,4-di-Cl-2-Me-benzyl | Me | H | 3,5-di-Me-morpholine | $CH_2$ | $CH_2$ |
| 2,4-di-F-benzyl | Me | H | 3,5-di-Me-morpholine | $CH_2$ | $CH_2$ |
| 4-t-Bu-2-CN-benzyl | Me | H | 3,4-di-Me-pyrrolidine | $CH_2$ | $CH_2$ |
| 4-[NCC(Me)$_2$]-phenyl | Me | H | pyrrolidine | $CH_2$ | $CH_2$ |
| 4-Me-1-pentynyl | Me | H | 3,5-di-Me-piperidine | $CH_2$ | O |

UNITED STATES PATENT AND TRADEMARK OFFICE
CERTIFICATE OF CORRECTION

PATENT NO. : 5,128,348
DATED : July 7, 1992
INVENTOR(S) : Gregory S. Basarab

It is certified that error appears in the above-identified patent and that said Letters Patent is hereby corrected as shown below:

| | | | | | |
|---|---|---|---|---|---|
| 2-Cl-4-t-BuPh | Me | H | 3,5-di-Me-piperidine | $CH_2$ | O |
| 2-OMe-4-t-BuPh | Me | H | 3,5-di-Me-piperidine | $CH_2$ | O |
| 2-F-4-i-Ph | Me | H | 3,5-di-Me-piperidine | $CH_2$ | O |
| 4-$CF_3$-Ph | Me | H | 3,5-di-Me-piperidine | $CH_2$ | O |
| 1-(4-t-BuPh)-ethenyl | Me | H | 3,5-di-Me-piperidine | $CH_2$ | O |
| 1-(4-t-BuPh)-ethenyl | Me | H | piperidine | $CH_2$ | O |
| 1-(4-t-BuPh)-ethenyl | Me | H | 3,5-di-Me-morpholine | $CH_2$ | $CH_2$ |
| 1-(4-t-BuPh)-ethenyl | Me | H | morpholine | $CH_2$ | $CH_2$ |
| 4-n-BuPh | H | H | piperidine | O | $CH_2$ |
| 4-t-Bu-cyclohexyl | H | H | piperidine | O | $CH_2$ |
| n-Bu | H | H | piperidine | O | $CF_2$ |
| cyclopentyl | H | H | piperidine | O | $CCl_2$ |
| 6-Me-hexyl | H | H | piperidine | S | $CH_2$ |
| 4-i-Pr-Ph | H | H | piperidine | S | $CH_2$ |
| 4-t-BuPh | Me | H | 3,5-di-Me-piperidine (N-oxide) | $CH_2$ | O |
| 4-t-BuPh | Me | H | 3,5-di-Me-piperidine (N-oxide) | $CH_2$ | $CH_2$ |
| 4-t-BuPh | Me | H | piperidine (N-oxide) | $CH_2$ | O |
| 4-t-BuPh | Me | H | piperidine (N-oxide) | $CH_2$ | $CH_2$ |
| 4-t-BuPh | Me | H | 3,5-di-Me-morpholine (N-oxide) | $CH_2$ | O |
| 4-t-BuPh | Me | H | 3,5-di-Me-morpholine (N-oxide) | $CH_2$ | CH2 |
| 4-t-BuPh | Me | H | perhydro-iso-quinoline (N-oxide) | $CH_2$ | $CH_2$ |

UNITED STATES PATENT AND TRADEMARK OFFICE
CERTIFICATE OF CORRECTION

PATENT NO. : 5,128,348
DATED : July 7, 1992
INVENTOR(S) : Gregory S. Basarab It is certified that error appears in the above-identified patent and that said Letters Patent is hereby corrected as shown below:

In Column 27 Claim 1, Formula I should read:

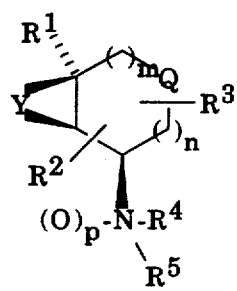

I

Signed and Sealed this

First Day of March, 1994

BRUCE LEHMAN

Attesting Officer          Commissioner of Patents and Trademarks